United States Patent [19]

Fischer et al.

[11] Patent Number: 4,513,150
[45] Date of Patent: Apr. 23, 1985

[54] PREPARATION OF BUT-2-ENE-1,4-DIONES SUBSTITUTED IN THE 1,4-POSITIONS

[75] Inventors: Rolf Fischer, Heidelberg; Hans-Martin Weitz, Bad Durkheim; Hardo Siegel, Speyer, all of Fed. Rep. of Germany

[73] Assignee: BASF Aktiengesellschaft, Ludwigshafen, Fed. Rep. of Germany

[21] Appl. No.: 592,908

[22] Filed: Mar. 23, 1984

[30] Foreign Application Priority Data

Mar. 29, 1983 [DE] Fed. Rep. of Germany ....... 3311320

[51] Int. Cl.$^3$ ............................................. C07C 45/59
[52] U.S. Cl. .................................... 568/385; 568/342; 568/386
[58] Field of Search .................. 508/385, 386, 342

[56] References Cited

U.S. PATENT DOCUMENTS 3,981,920 9/1976 Buchi ................ 568/386
4,340,764 7/1982 Milner ............... 568/386

FOREIGN PATENT DOCUMENTS 2092571 8/1982 United Kingdom ........... 568/386
833965 4/1981 U.S.S.R. ........................ 568/386

OTHER PUBLICATIONS

Williams et al., J. Org. Chem., vol. 46, pp. 4143–4147, (1981).
Ramadas et al., Org. Prep. Proced. Int., vol. 13, pp. 9–12, (1981).
Bull. Soc. Chim., France 1957, 977–1003.
Acta Chem. Scand. 1, (1947), 419–420.
Comptes Rendus Acad. Sciences Paris, 258, (1964), 4094–4096.
Rec. trac. chim. 50, (1931), 1029–1034.
Chem. Ber. 96, (1963), 2712–2722.

*Primary Examiner*—James H. Reamer
*Attorney, Agent, or Firm*—John H. Shurtleff

[57] ABSTRACT

But-2-ene-1,4-diones substituted in the 1,4-positions, of the formula

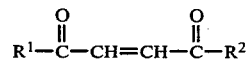

where $R^1$ and $R^2$ are each an aliphatic hydrocarbon radical of 1 to 17 carbon atoms, are prepared by a process in which a 2,5-disubstituted furan of the formula

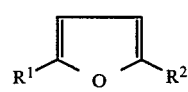

where $R^1$ and $R^2$ have the above meaning, is oxidized with a percarboxylic acid in the presence of a carboxylic acid.

6 Claims, No Drawings

PREPARATION OF BUT-2-ENE-1,4-DIONES SUBSTITUTED IN THE 1,4-POSITIONS

The present invention relates to a process for the preparation of but-2-ene-1,4-diones substituted in the 1,4-positions, by oxidizing a 2,5-disubstituted furan with an aliphatic percarboxylic acid.

A number of routes for the preparation of 1,4-dialkyl-but-2-ene-1,4-diones from 2,5-dialkylfurans are known. For example, hex-3-ene-2,5-dione can be prepared by oxidizing 2,5-dimethylfuran with a complex obtained from chromyl chloride and pyridine (German Laid-Open Application DOS 3,136,987), or by hydrolyzing 2,5-dimethoxy-2,5-dimethyl-2,5-dihydrofuran, which is obtainable from 2,5-dimethylfuran (Bull. Soc. Chim. France 1957, 997–1003). 2,2,7,7-Tetramethyloct-4-ene-3,6-dione can be obtained by reacting 2,5-di-tert.-butylfuran with an inorganic hypochlorite (European Pat. No. 32,290).

These processes have the disadvantages that several reaction steps are required, toxic oxidizing agents are used and/or neutral salts are obtained in the reaction and have to be disposed of.

We have found that but-2-ene-1,4-diones which are substituted in the 1,4-positions, of the formula

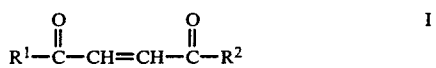

where $R^1$ and $R^2$ are each an aliphatic hydrocarbon radical of 1 to 17 carbon atoms, can be prepared in a substantially more advantageous manner by oxidizing a 2,5-disubstituted furan of the formula

where $R^1$ and $R^2$ have the above meaning, if the oxidation is carried out using an aliphatic percarboxylic acid and in the presence of an aliphatic carboxylic acid.

For the oxidation of 2,5-dimethylfuran with peracetic acid in acetic acid to give hex-3-ene-2,5-dione, the reaction can be represented by the following equation:

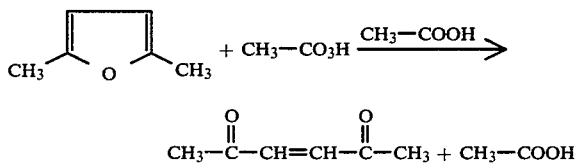

The result of the process could not be foreseen, since the reaction of furan with peracetic acid or perbenzoic acid gives malealdehyde in poor yield (Acta Chem. Scand. 1, 1947, 419–420). If furan is oxidized with p-nitroperbenzoic acid in ether, 3-formylacrylic acid is isolated in a yield of only 12% (Comptes rendues Acad. Sciences Paris 258 (1964), 4094–4096). In contrast, the reaction of 2-methylfuran with peracetic acid in glacial acetic acid gives small amounts of 3-hydroxy-5-methyl-2(2,3H)furanone, 90% of the 2-methylfuran used being converted to resin-like products (Rec. trac. chim. 50 (1931), 1029–1034. The data on the reaction of alkylfurans with hydrogen peroxide provide just as poor a basis for predicting the process according to the invention. For example, the treatment of 2-methylfuran with hydrogen peroxide in the presence of sodium stannate gives 5-methyl-2(5H)-furanone (U.S.S.R. Pat. No. 833,965), or the reaction of 2,5-dimethylfuran with hydrogen peroxide gives three different cyclic bishydroperoxides, depending on the reaction conditions (Chem. Ber. 96 (1963), 2712–2722).

In formulae I and II, $R^1$ and $R^2$ are each aliphatic hydrocarbon radicals, such as alkyl or cycloalkyl radicals of 1 to 17 carbon atoms, eg. methyl, ethyl, n-propyl, i-propyl, n-butyl, i-butyl, sec.-butyl, tert.-butyl, hexyl, octyl, palmityl, stearyl, cyclopentyl, cycloheptyl or cyclohexyl.

The starting materials of the formula II can be prepared by, for example, intramolecular condensation of a 1,4-dialkylbut-2-ane-1,4-dione in the presence of a mineral acid (German Laid-Open Application DOS 2,013,261) or of an acidic ion exchanger (J. Org. Chem. 45, 5048–5052), or by catalytic hydrogenation of a 5-alkylfurfural (U.S.S.R. Pat. No. 844,617). Examples of starting materials of the formula II are 2,5-dimethylfuran, 2-methyl-5-ethylfuran, 2,5-di-tert.-butylfuran, 2,5-dicyclohexylfuran, 2,5-dipalmitylfuran and 2-methyl-5-cyclopentylfuran.

The oxidizing agents used are aliphatic percarboxylic acids, such as those of the formula $R^3$—$CO_3H$ (III), and the aliphatic carboxylic acids used are, for example, those of the formula $R^4$—COOH (IV). $R^3$ and $R^4$ are each alkyl or cycloalkyl of 1 to 17 carbon atoms, preferably alkyl of 1 to 5 carbon atoms.

Examples of suitable percarboxylic acids of the formula III are performic acid, peracetic acid, perpropionic acid, per-n-butyric acid and per-i-butyric acid. The peroxy acids need not be used in the anhydrous form, but may also be employed in the form of, for example, a water-containing equilibrium peroxy acid. To prepare the equilibrium peroxy acid, an aliphatic carboxylic acid, eg. acetic acid, is reacted with 50% strength hydrogen peroxide in the presence of concentrated sulfuric acid as a catalyst. The sulfuric acid is neutralized before the peroxy acid is used.

Examples of suitable carboxylic acids of the formula IV are formic acid, acetic acid, propionic acid, butyric acid, valeric acid, capric acid, lauric acid, oleic acid, palmitic acid and cyclohexanecarboxylic acid. For economic reasons, acetic acid is particularly preferred. The carboxylic acid is generally added in excess, for example in an amount of from 1 to 80 moles per mole of the furan compound II used.

The reaction of the furan with the percarboxylic acid in the presence of the carboxylic acid is carried out, for example, using from 1 to 80, in particular from 1.5 to 60, moles of the carboxylic acid and from 0.5 to 2, in particular from 1 to 1.5, moles of the percarboxylic acid per mole of the furan compound. The reaction is advantageously carried out at from 0° to 200° C., in particular from 20° to 120° C., usually either in an excess of the carboxylic acid as a solvent or in the presence of an additional solvent which is inert under the reaction conditions. Examples of suitable solvents of this type are carboxylates, eg. methyl acetate, chlorohydrocarbons, eg. methylene chloride, chloroform, carbon tetrachloride or 1,2-dichloroethane, hydrocarbons, eg. alkanes, benzene or alkylbenzenes, and ethers, eg. diethyl ether, tetrahydrofuran or dioxane. Advantageously, from 0.1 to 80, in particular from 2 to 60, moles of the said inert solvent are used per mole of starting compound II.

The novel process can be carried out batchwise or continuously, under atmospheric or superatmospheric pressure. Unreacted furan of the formula II can, if desired, be separated off from the resulting but-2-ene-1,4-dione of the formula I after the reaction by distillation, and can be reused for the reaction according to the invention.

In the batchwise procedure, the reaction is carried out, for example, as follows: the percarboxylic acid is added to a solution of the furan compound in the carboxylic acid at the reaction temperature and under the reaction pressure, the said solution also containing the solvent where relevant. When the addition is complete, stirring is continued, if necessary. The mixture is monitored for unreacted peroxy compound, and the solvent and/or the carboxylic acid are distilled off, after which fractional distillation or recrystallization is carried out. In the distillation, unreacted starting compounds are, if required, separated off from the desired but-2-ene-1,4-dione.

The but-2-ene-1,4-diones substituted in the 1,4-positions are obtained as mixtures of the E and Z isomers. The E isomers can be converted to the Z isomers by irradiation (German Laid-Open Application DOS 3,136,987), and the Z isomers can be converted to the E isomers by, for example, heating with iodine (J. Heterocycl. Chem. (1972), page 528), so that the particular isomer desired can be obtained from the resulting isomer mixture.

The 1,4-dialkylbut-2-ene-1,4-diones II obtainable by the novel process are useful intermediates and can be used, for example, for the preparation of pyridazines (J. Heterocycl. Chem. (1972), pages 523–529), as well as for the preparation of retrolones, which are employed for the synthesis of the insecticidal pyrethrins (German Laid-Open Applications DOS 2,819,879 and DOS 3,136,987).

Using the process of the invention, the desired but-2-ene-1,4-diones substituted in the 1,4-positions are obtained smoothly and by a simple route. Because readily available starting materials are used and toxic oxidizing agents are avoided, the process is very suitable for use on an industrial scale. The production of salts, and the disposal problems associated with this, are likewise avoided.

EXAMPLE 1

34.2 g of anhydrous peracetic acid (12% by weight) in glacial acetic acid (prepared as described in Houben-Weyl, 4th Edition, Methoden der organischen Chemie, Volume 8, page 41) were added dropwise to a solution of 4.3 g of 2,5-dimethylfuran in 5 g of glacial acetic acid at 40° C. in the course of 20 minutes, while stirring and cooling. Stirring was continued for 30 minutes at 40° C., after which, according to iodometric titration, only 1.5 mole % of the initial amount of peracetic acid was still present in the reaction mixture.

The glacial acetic acid was stripped off in a rotary evaporator, and the residue was subjected to bulb tube distillation (60°–100° C./0.7 mbar) to give 3.4 g (68%, based on 2,5-dimethylfuran used) of liquid hex-3-ene-2,5-dione; $n_D^{20}=1.4560$.

$^1$H-NMR spectrum (CDCl$_3$): Z-hex-3-ene-2,5-dione: $\delta=2.20$ (s, 6H), 6.30 (s, 1H); E-hex-3-ene-2,5-dione: $\delta=2.35$ (s, 6H), 6.75 (s, 1H)

The ratio of the methyl protons to the olefinic protons shows that a mixture consisting of 75% of Z- and 25% of E-hex-3-ene-2,5-dione was obtained.

EXAMPLE 2

A mixture of 500 g of glacial acetic acid, 52 g of 50% strength hydrogen peroxide and 2.5 g of concentrated sulfuric acid was stirred for 48 hours at room temperature. 2.8 g of potassium acetate were added, shortly before the reaction with 2,5-dimethylfuran, to 260 g of the equilibrium peracetic acid prepared in this manner, in order to neutralize sulfuric acid.

260 g of the equilibrium peracetic acid (10.5% by weight) were added to a stirred solution of 29 g of 2,5-dimethylfuran in 30 g of glacial acetic acid at 40° C. in the course of 35 minutes, while cooling. Stirring was continued for 20 minutes at 40° C. The residual content of peracetic acid, which was determined as described in Example 1, was 1.4 mole %, based on peracetic acid used. The $^1$H-NMR spectrum of the reaction mixture showed no evidence of the existence of cyclic peroxides, as observed in the reaction of 2,5-dimethylfuran with 80–90% strength hydrogen peroxide (Chem. Ber. 96 (1963), 2712–2722).

The acetic acid was stripped off in a rotary evaporator, the precipitated potassium sulfate was filtered off and the filtrate was distilled to give 21.3 g (63%, based on 2,5-dimethylfuran used) of hex-3-ene-2,5-dione of boiling point 95°–100° C./17 mbar. The $^1$H-NMR spectrum shows that the isomer mixture consists of 30% of Z- and 70% of E-hex-3-ene-2,5-dione.

We claim:

1. A process for the preparation of a but-2-ene-1,4-dione substituted in the 1,4-positions, of the formula

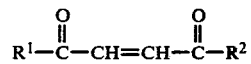

where $R^1$ and $R^2$ are each an aliphatic hydrocarbon radical of 1 to 17 carbon atoms, by oxidizing a 2,5-disubstituted furan of the formula

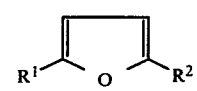

where $R^1$ and $R^2$ have the above meaning, wherein the oxidation is carried out using an aliphatic percarboxylic acid and in the presence of an aliphatic carboxylic acid at from 0° to 200° C.

2. A process as claimed in claim 1, wherein the aliphatic percarboxylic acid of the formula $R^3$—CO$_3$H and an aliphatic carboxylic acid of the formula $R^4$—COOH, in which $R^3$ and $R^4$ are each an alkyl or cycloalkyl radical of 1 to 17 carbon atoms, are used.

3. A process as claimed in claim 1, wherein the percarboxylic acid used is performic acid, peracetic acid, perpropionic acid, per-n-butyric acid or per-i-butyric acid.

4. A process as claimed in claim 1, wherein the carboxylic acid used is formic acid, acetic acid, butyric acid, propionic acid, valeric acid, lauric acid, oleic acid, palmitic acid or cyclohexanecarboxylic acid.

5. A process as claimed in claim 1 wherein the percarboxylic acid used is peracetic acid.

6. A process as claimed in claim 1 wherein the carboxylic acid used is acetic acid.

* * * * *